(12) United States Patent
Iacoangeli et al.

(10) Patent No.: US 9,416,116 B2
(45) Date of Patent: Aug. 16, 2016

(54) METHOD OF PREPARATION OF METAXALONE

(71) Applicant: AZIENDE CHIMICHE RIUNITE ANGELINI FRANCESCO A.C.R.A.F. S.p.A., Rome (IT)

(72) Inventors: Tommaso Iacoangeli, Rome (IT); Mario Chiavarini, Rome (IT); Antonello Fazio, Latina (IT); Marcello Marchetti, Rome (IT); Giovanni Battista Ciottoli, Rome (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 14/742,203

(22) Filed: Jun. 17, 2015

(65) Prior Publication Data

US 2015/0284345 A1    Oct. 8, 2015

Related U.S. Application Data

(62) Division of application No. 13/990,974, filed as application No. PCT/EP2012/050609 on Jan. 17, 2012, now abandoned.

(60) Provisional application No. 61/439,127, filed on Feb. 3, 2011.

(30) Foreign Application Priority Data

Feb. 1, 2011    (EP) .................................... 11152849

(51) Int. Cl.
| | | |
|---|---|---|
| C07D 263/24 | (2006.01) | |
| C07D 405/06 | (2006.01) | |
| C07D 405/14 | (2006.01) | |

(52) U.S. Cl.
CPC ............. *C07D 263/24* (2013.01); *C07D 405/06* (2013.01); *C07D 405/14* (2013.01)

(58) Field of Classification Search
None
See application file for complete search history.

(56) References Cited

U.S. PATENT DOCUMENTS

| 6,562,980 B1 | 5/2003 | Lee et al. |
| 2007/0185177 A1 | 8/2007 | Chattopadhyay et al. |

FOREIGN PATENT DOCUMENTS

| FR | 1 487 641 | 7/1966 |
| WO | 03 061552 | 7/2003 |
| WO | 2008 006096 | 1/2008 |

OTHER PUBLICATIONS

Akerlof, A., "Dielectric Constants of Some Organic Solvent-Water Mixtures at Various Temperatures", The Journal of the American Chemical Society, vol. 54, No. 11, pp. 4125-4139, (Nov. 1, 1932), XP055001175.

Leader, G. R. et al., "The Dielectric Constant of N-Methylamides", The Journal of the American Chemical Society, vol. 73, No. 12, pp. 5731-5733, (Dec. 19, 1951), XP055001179.

International Search Report Issued Feb. 28, 2012 in PCT/EP12/050609 Filed Jan. 17, 2012.

*Primary Examiner* — Alicia L Otton
(74) *Attorney, Agent, or Firm* — Oblon, McClelland, Maier & Neustadt, L.L.P.

(57) ABSTRACT

The present invention relates to a method of preparation of metaxalone comprising reaction of triglycidyl isocyanurate (TGIC) with m-xylenol, characterized in that said reaction is carried out in a solvent mixture comprising an aprotic polar solvent with dielectric constant greater than or equal to 30 and at least one other solvent selected from the group comprising apolar solvents and aprotic polar solvents with dielectric constant below 30 said solvent mixture comprising from 5 to 40 wt. % of said first solvent and from 95 to 60 wt. % of said second solvent, adding the TGIC at a temperature between 30° C. and 50° C., and after adding the TGIC, raising the temperature of the reaction solution to a value between 80° C. and 180° C. in a time between 120 and 180 minutes at a rate of increase not greater that 1.25° C. per minute. The invention also relates to a metaxalone with a reduced content of impurities derived from incomplete reactions and/or side reactions of the method of production.

20 Claims, No Drawings

METHOD OF PREPARATION OF METAXALONE

FIELD OF THE INVENTION

The present invention relates to a method of preparation of metaxalone.

In particular, the present invention relates to an improved method for preparing metaxalone that comprises the reaction between triglycidyl isocyanurate and 3,5-dimethylphenol.

Moreover, the present invention also relates to metaxalone with a reduced content of impurities derived from incomplete reactions and/or side reactions of the method of production.

PRIOR ART

Metaxalone is a muscle relaxant used for relaxing muscles and alleviating pain caused by strains, sprains, and other musculoskeletal pathological conditions. Its precise mechanism of action is not known, but it may be due to general depression of the central nervous system. It is regarded as a moderately strong muscle relaxant, with a relatively low incidence of side effects.

Metaxalone (MW:221) is the common name of 5-[(3,5-dimethylphenoxy)methyl]-1,3-oxazolidin-2-one having the following structural formula (I):

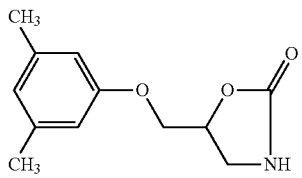
(I)

Patent FR 1,487,641 describes a method of preparation of 5-aryloxymethyl-2-oxazolidones and 5-arylthiomethyl-2-oxazolidones comprising reaction between triglycidyl isocyanurate (TGIC) and, respectively, phenols or thiophenols at a temperature between 60° C. and 230° C. optionally in the presence of a proton acceptor, i.e. an inorganic or organic base, and/or organic solvents, for example benzene, toluene, chlorobenzene, dimethylformamide (DMF), dimethylsulphoxide (DMSO), acetone, acetophenone, benzophenone, benzonitrile and acetonitrile.

In the method described in example 7 of patent FR 1,487,641, metaxalone is prepared by reacting TGIC (MW:297) with m-xylenol (the common name of 3,5-dimethylphenol—MW:122) in chlorobenzene under reflux with a molar ratio of TGIC to m-xylenol of about 1:3. The method described envisages the use of 300 ml of solvent (chlorobenzene) per 29.7 g of TGIC, equal to 3 liters of solvent per mole of TGIC. The reaction is completed in a period of time of 13 hours with a yield of about 74 wt. %.

U.S. Pat. No. 6,562,980 describes a method of preparation of 5-aryloxymethyl-2-oxazolidones of general formula

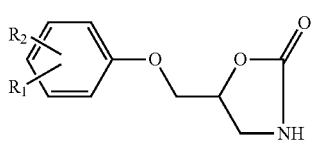
(II)

where $R_1$ and $R_2$ can be a hydrogen atom or a halogen atom, or a linear or branched alkyl or alkoxy group with not more than 3 carbon atoms.

The method described in U.S. Pat. No. 6,562,980 envisages reacting triglycidyl isocyanurate (TGIC) with a suitable phenol. In particular, the method envisages reacting triglycidyl isocyanurate (TGIC) of formula (III)

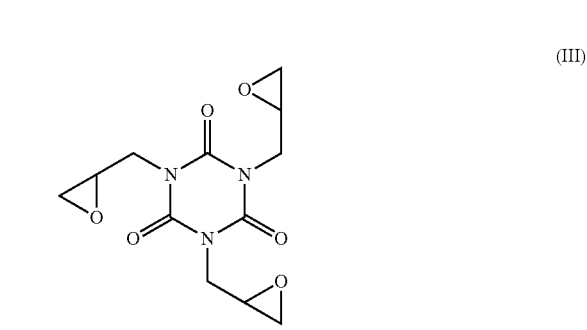 [SMILES: O=c1n(CC2CO2)c(=O)n(CC2CO2)c(=O)n1CC1CO1]
(III)

with a phenol of formula (IV)

(IV)

where $R_1$ and $R_2$ have the meanings given above.

In particular, the single preparative example of U.S. Pat. No. 6,562,980 describes the preparation of metaxalone by reaction between TGIC and 3,5-dimethylphenol (m-xylenol).

The reaction is carried out in a solvent under reflux with a molar ratio of TGIC to m-xylenol of about 1:3. The preferred solvent is acetone, which can be used in combination with water, but the possibility of using ethanol, ethyl acetate and chloroform is described.

Preferably, the reaction is carried out in the presence of a base, such as NaOH or $NH_4OH$, in a nitrogen atmosphere. The reaction is completed in a period of time between 10 and 60 hours, preferably from 12 to 24 hours.

According to U.S. Pat. No. 6,562,980, in the reaction each of the hydroxyl groups of the phenol reacts with one of the three epoxypropyl groups, which in their turn react with the amide group of the isocyanurate to form the 1,3-oxazolidin-2-one ring.

The example in U.S. Pat. No. 6,562,980 describes the use of 50 ml of solvent (acetone) per 10 mmol of TGIC (equal to about 5 liters of solvent per mole of TGIC) and 1.2 grams of base (NaOH) per 10 mmol of TGIC (equal to about three moles of base per mole of TGIC).

BRIEF DESCRIPTION OF THE INVENTION

The applicant noticed that the methods of preparation described in the prior art have various disadvantages.

Firstly, the applicant noticed that the methods of preparation described in the prior art are not compatible with the requirements of high productivity and low cost that are now specified for the industrial production of this type of product.

In fact, the reaction times between 12 and 24 hours require the use of plant for two or three shifts, or even more. Moreover, the use of large amounts of solvent and of base means high costs of raw materials, high costs for separation and high costs for disposal.

Furthermore, the applicant found that the yield of the method of reaction described in the aforementioned U.S. Pat. No. 6,562,980 is below 30%. In fact, the yield of 81% declared in U.S. Pat. No. 6,562,980 is a molar yield (1.8 g of metaxalone is equivalent to about 8.1 mmol), incorrectly calculated as it refers to the molar amount of TGIC used (10 mmol) without taking into account that from 1 mole of TGIC it is theoretically possible to obtain 3 moles of metaxalone. The true molar yield, equivalent to the yield by weight, obtained by the method of reaction described in the aforementioned U.S. Pat. No. 6,562,980 is therefore about 27%.

Finally, the applicant found that the methods of preparation described in the prior art cause the formation of (i) genotoxic impurities comprising epoxide groups represented by compounds derived from incomplete reaction between TGIC and m-xylenol and/or from the TGIC itself and (ii) impurities derived from the side reaction between the metaxalone already formed and the residual TGIC present in the reaction solution.

The applicant therefore dealt with the problem of developing a novel method of preparation of metaxalone capable of overcoming the aforementioned disadvantages.

The applicant found a novel method of preparation of metaxalone that greatly improves, on the one hand, the industrial productivity, with a reduction in the times and costs of reaction of the new process relative to the processes known hitherto, and, on the other hand, the yield and quality of the reaction product.

The applicant surprisingly found that metaxalone can easily be obtained with reaction times of less than ten hours, preferably less than eight hours, and in particular of about five hours, by reacting triglycidyl isocyanurate (TGIC) with m-xylenol in a solvent mixture comprising an aprotic polar solvent with dielectric constant greater than or equal to 30 and at least one other solvent selected from the group comprising apolar solvents and aprotic polar solvents with dielectric constant below 30, preferably below 25, and by raising the temperature of the reaction solution to a value between 80° C. and 180° C., preferably between 100° C. and 160° C., in a time between 120 and 180 minutes, with a rate of temperature increase preferably not greater than 1.25° C./min.

The applicant surprisingly found that by working in the aforementioned conditions, the volumes of solvent and the amounts of base used could be reduced considerably. In particular, the amount of solvent used can be less than 1 liter per mole of TGIC and the amount of base can be less than one tenth of a mole per mole of TGIC.

Therefore, the present invention relates to a method of preparation of metaxalone having the following structural formula (I):

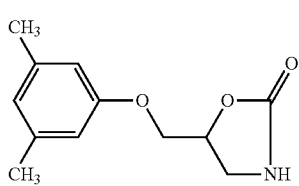

comprising reaction of triglycidyl isocyanurate (TGIC) of formula (III)

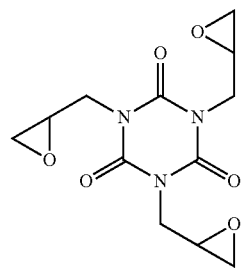

with m-xylenol of formula (V)

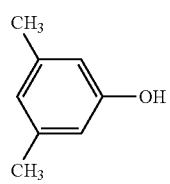

characterized in that said reaction is carried out in a solvent mixture comprising a first solvent selected from the group comprising aprotic polar solvents with dielectric constant greater than or equal to 30 and a second solvent selected from the group comprising apolar solvents and aprotic polar solvents with dielectric constant below 30, preferably below 25, said solvent mixture comprising from 5 to 40 wt. % of said first solvent and from 95 to 60% wt. % of said second solvent, adding the TGIC at a temperature between 30° C. and 50° C. and, after adding the TGIC, raising the temperature of the reaction solution to a value between 80° C. and 180° C. in a time between 120 and 180 minutes at a rate of increase not greater that 1.25° C. per minute.

Moreover, the applicant surprisingly found that the metaxalone obtained by the process of the present invention has a reduced content of impurities, and in particular of (i) genotoxic impurities containing epoxide groups represented by compounds derived from incomplete reaction between TGIC and m-xylenol and/or by TGIC itself and (ii) impurities derived from the side reaction between the metaxalone already formed and the residual TGIC present in the reaction solution.

Therefore, the present invention also relates to metaxalone comprising less than 1 ppm of (i) genotoxic impurities containing epoxide groups and/or less than 500 ppm of (ii) impurities derived from the side reaction between the metaxalone already formed and the residual TGIC present in the reaction solution.

DETAILED DESCRIPTION OF THE INVENTION

In the process of preparation of the present invention, the reaction is carried out in a solvent mixture comprising an aprotic polar solvent with dielectric constant greater than or equal to 30 and at least one other solvent selected from the group comprising apolar solvents and aprotic polar solvents with dielectric constant below 30, preferably below 25.

The dielectric constant, also known as relative permittivity, is a property of an electrical insulating material (a dielectric). The dielectric constant, as employed herein, is equal to the ratio of the capacitance of a capacitor filled with the given material to the capacitance of an identical capacitor in a vacuum without the dielectric material. If C is the value of the capacitance of a capacitor filled with a given dielectric and $C_0$ is the capacitance of an identical capacitor in a vacuum, the dielectric constant, symbolized by the Greek letter kappa, κ, is simply expressed as $κ=C/C_0$. Dielectric constant is a number without dimensions. For the purpose of the present description and claims the dielectric constant values of the solvents used in the present invention have been obtained at 20° C. and can be generally found in chemical handbooks, such as, for example, in "Handbook of Chemistry and Physics", David R. Lide, CRC, $83^{rd}$ Edition, 2002-2003.

The aprotic polar solvent with dielectric constant (d.c.) greater than or equal to 30 preferably used in the process of preparation of the present invention is selected from N-methylpyrrolidone (NMP—d.c.=32.55), dimethylformamide (DMF—d.c.=38.25), dimethylsulphoxide (DMSO—d.c.=47.24), hexamethylphosphoramide (HMPA—d.c.=31.3), dimethylacetamide (d.c.=38.85) and acetonitrile (d.c.=36.64).

Advantageously, the aprotic polar solvent is selected from N-methylpyrrolidone (NMP) and dimethylformamide (DMF).

The apolar solvent preferably used, in combination with the aprotic polar solvent described above, in the method of preparation of the present invention is selected from cyclohexane, heptane, benzene, toluene, xylene, mesitylene, naphthalene, chlorobenzene, chloroxylene, chloroform, propyl ether, isopropyl ether, butyl ether, pentyl ether, benzylethyl ether, tetrahydrofuran (THF) and 2-methyl tetrahydrofuran.

The aprotic polar solvent with dielectric constant below 30 preferably used, in combination with the aprotic polar solvent described above, in the method of preparation of the present invention is selected from acetone (d.c.=21.01), methyl ethyl ketone (d.c.=18.56), methyl butyl ketone (d.c.=14.56), methyl isobutyl ketone (d.c.=13.11), 2-pentanone (d.c.=15.45), cyclopentanone (d.c.=13.58) and 2-heptanone (d.c.=11.95).

Advantageously, the apolar solvent is selected from the group comprising aromatic hydrocarbons, in particular toluene and xylene, and the aprotic polar solvent with dielectric constant below 30 is selected from the group comprising ketones, in particular methyl isobutyl ketone (MIK).

Preferably, the solvent mixture comprises from 10 to 30 wt. %, of aprotic polar solvent with dielectric constant greater than or equal to 30.

Advantageously, the solvent mixture comprises from 90 to 70 wt. %, of apolar solvent and/or of aprotic polar solvent with dielectric constant below 30.

The solvent mixture used in the process of the present invention has a boiling point between 80° C. and 180° C.

In the process of preparation of the present invention the reaction solution comprises triglycidyl isocyanurate (TGIC) having the aforementioned formula (III) and m-xylenol having the aforementioned formula (V) dissolved in the aforementioned solvent mixture.

Preferably, the amount of solvent mixture used is less than 1 liter per mole of TGIC.

The stoichiometry of reaction between m-xylenol and TGIC requires three moles of m-xylenol per mole of TGIC. In the process of preparation of the present invention the reaction solution comprises the stoichiometric amount of m-xylenol and TGIC.

Advantageously, the reaction solution further comprises a base and a phase transfer catalyst.

The base can be an organic or inorganic base. Preferably the inorganic base can be represented by oxides or hydroxides of alkali metals, such as NaOH, KOH, LiOH, or by carbonates of alkali metals or alkaline earth metals, such as $Ca_2CO_3$, $K_2CO_3$. The organic base can be triethylamine (TEA), diazobicycloundecene (DBU), dibutylamine (DBA), and so on. Advantageously, the base is an inorganic base represented by oxides or hydroxides of alkali metals, in particular NaOH and KOH.

The amount of base added to the reaction solution, before adding TGIC, is between 3 and 10 mol. %, preferably between 3 and 6 mol. %, relative to the molar amount of TGIC present in the same reaction solution.

The phase transfer catalyst is a compound that promotes reaction between compounds in different phases. Typically, these compounds are represented by salts, in particular halides, of quaternary ammonium or phosphonium. Examples of phase transfer catalysts for use in the process of the present invention are represented by methyltriethylammonium chloride, tetrabutylammonium chloride, tetraethylammonium chloride, tetraethylammonium bromide, tetramethylammonium bromide, tetramethylammonium chloride, tetrapropylammonium bromide, triethylmethylammonium chloride, trimethylphenylammonium chloride, trimethylphenylammonium bromide, trimethylbenzylammonium bromide, trimethylbenzylammonium chloride, triethylbenzylammonium chloride, triethylbenzylammonium bromide, tributylbenzylammonium chloride, tributylbenzylammonium bromide, (1-butyl)triethylammonium bromide, dodecyltrimethylammonium bromide, dodecyltrimethylammonium chloride, tetra-n-butylphosphonium bromide, tetraphenylphosphonium bromide. Advantageously, the phase transfer catalyst used in the process of preparation of the present invention is triethylbenzylammonium chloride (TEBAC).

The amount of phase transfer catalyst added to the reaction solution is between 0.5 and 5 mol. %, preferably between 1 and 3 mol. % relative to the amount of TGIC present in said reaction solution.

In the process of preparation of the present invention the solution comprising m-xylenol, the base and the phase transfer catalyst dissolved in the solvent mixture is preferably heated to a temperature between 30° C. and 50° C., preferably between 35° C. and 45° C., before adding the TGIC.

After adding the TGIC, the reaction solution is gradually heated until it reaches a reaction temperature between 80° C. and 180° C. in a time between 120 and 180 minutes.

Preferably, the reaction solution is gradually heated until it reaches a reaction temperature between 100° C. and 160° C., and in particular between 115° C. and 145° C.

Advantageously, the reaction solution is gradually heated at a rate of increase preferably not greater than 1.00° C. per minute, and more preferably not greater than 0.75° C. per minute.

The method of raising the temperature can envisage one or more pauses at intermediate constant temperatures. For example, if the temperature to be reached is 140° C., a pause can be envisaged at a temperature between 90° C. and 110° C., or two pauses at a temperature between 80° C. and 100° C. and between 100° C. and 120° C. respectively, or three pauses at a temperature between 60° C. and 80° C., between 80° C. and 100° C. and between 100° C. and 120° C. respectively. The length of pause can vary in the range between 10 and 60 minutes.

At the end of the temperature increase phase, an amount of base between 3 and 10 mol. %, preferably between 5 and 8 mol. %, relative to the molar amount of TGIC present in the starting reaction solution, is again added to the reaction solution.

The reaction temperature is preferably maintained for a reaction time between 60 and 120 minutes.

The reaction between m-xylenol and TGIC envisages reaction between the hydroxyl of the m-xylenol and the epoxide ring of the TGIC. In particular, three molecules of m-xylenol react with three epoxypropyl groups of TGIC to form the compound of formula (VI).

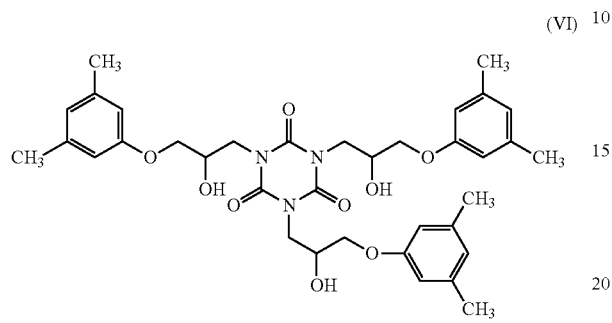

(VI)

Finally, it is considered that the three hydroxyl groups of compound (VI) react with the amide group of the isocyanurate ring, which then undergoes a rearrangement that leads to formation of the oxazolidin-2-one ring, and consequently to the formation of three molecules of metaxalone having the aforementioned formula (I).

The applicant noticed that the methods of preparation described in the prior art lead to the formation of (i) genotoxic impurities represented by compounds derived from incomplete reaction between TGIC and m-xylenol and/or from the TGIC itself and (ii) impurities derived from the side reaction between the metaxalone already formed and the residual TGIC present in the reaction solution.

With regard to the impurities (i), the applicant observed that the reaction of formation of the compound of formula (VI) comprises intermediate phases of reaction of TGIC with one or two molecules of m-xylenol that lead to the formation of the following compounds of formula (VII) and (VIII).

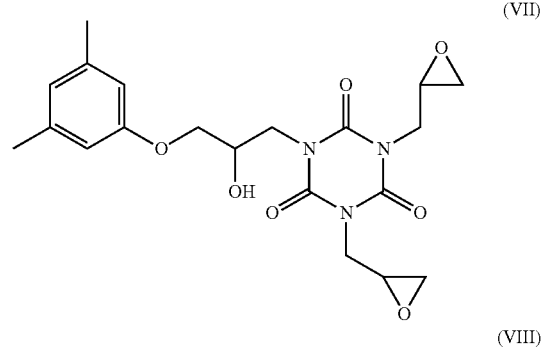

(VII)

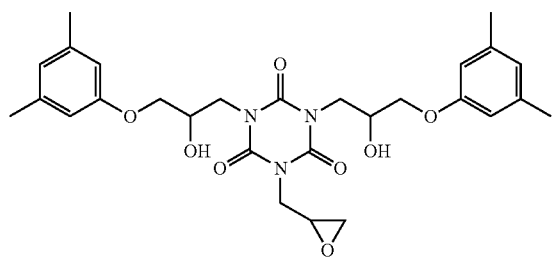

(VIII)

The applicant found that, in the reaction conditions described in the prior art, the compounds of formula (VII) and (VIII), as well as the TGIC itself, remain present as impurities in the metaxalone final product. Owing to the presence of the epoxypropyl groups, the compounds of formula (VII) and (VIII) and the TGIC itself are considered to be genotoxic impurities.

With regard to the impurities (ii), reaction between the metaxalone already formed and the epoxide groups still present in the reaction mixture, for example, epoxide groups of the TGIC or of the compounds of formula (VII) and (VIII), leads to formation of the compound of formula (IX).

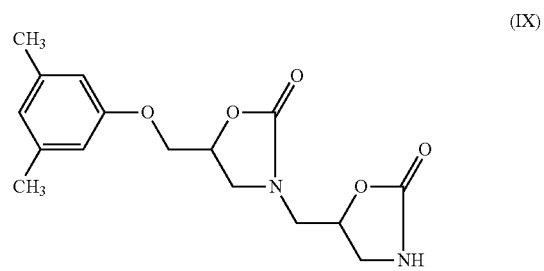 [SMILES: Cc1cc(C)cc(OCC2CN(CC3CNC(=O)O3)C(=O)O2)c1]

(IX)

The applicant found that in the method of preparation of the present invention, the presence of the solvent mixture and the gradual heating of the reaction solution promotes completion of the reaction between m-xylenol and TGIC to form the compound of formula (VI).

The subsequent addition of base and maintaining the reaction temperature then promotes the final rearrangement of the compound of formula (VI) to form metaxalone, as described above.

At the end of the reaction time the reaction solution is then preferably cooled to a temperature between 0° C. and 20° C. to promote crystallization of the product, which is then separated and washed by conventional techniques, optionally with the aid of suitable solvents, for example the same solvents as described previously, in particular toluene, xylene and MIK.

In this way, the method of preparation of the present invention, as well as using a smaller amount of solvents and base, guarantees a higher yield and better quality of the metaxalone final product.

In particular, the method of preparation of the present invention makes it possible to obtain a yield of metaxalone greater than or equal to 60 wt. % relative to that theoretically obtainable, with a quality greater than or equal to 99.8%.

In particular, the metaxalone finished product prepared according to the method of preparation of the present invention contains an amount of genotoxic impurities containing epoxides represented by unreacted TGIC and compounds of formula (VII) and (VIII) below 1 ppm, preferably below 0.5 ppm, and even more preferably below 0.1 ppm.

Therefore, a further aspect of the present invention relates to metaxalone comprising less than 1 ppm of genotoxic impurities containing epoxides represented by TGIC and the compounds of formula (VII) and (VIII) described above.

Preferably, the metaxalone of the present invention comprises less than 0.5 ppm, and even more preferably less than 0.1 ppm, of genotoxic impurities containing epoxides represented by TGIC and compounds of formula (VII) and (VIII) described above.

Moreover, the metaxalone of the present invention comprises less than 500 ppm, preferably less than 300 ppm, and even more preferably less than 100 ppm, of impurities derived from the side reaction between the metaxalone already formed and the residual TGIC present in the reaction solution, for example the compound of formula (IX) described above.

The following examples aim to illustrate the present invention but without limiting it in any way.

EXPERIMENTAL PART

Example 1

Preparation of Metaxalone in Methyl Isobutyl Ketone (MIK) and N-Methylpyrrolidone (NMP)

A 1-liter round-bottom flask was charged with about 180 ml of MIK, 101 g of m-xylenol, 20 ml of NMP, 1.0 g of triethylbenzylammonium chloride (TEBAC) and 0.40 g of NaOH. The reaction solution was heated to about 40° C. and kept at this temperature for about 30 minutes.

Then, 82 g of triglycidyl isocyanurate (TGIC) were added and the reaction solution was heated to 100° C. in about 3 hours, with a constant rate of temperature increase of about 0.33° C./min.

After that time, further 0.8 g of NaOH were added to the reaction solution, it was heated to 120° C. with a constant rate of temperature increase of about 1.00° C./min, and kept at this temperature for about 90 minutes.

Then, the reaction solution was diluted with about 70 ml of MIK, and cooled to a temperature between 0° and 5° C. The product metaxalone was recovered by filtration, and purified by treatment with about 360 ml of MIK at 40° C.

The metaxalone thus obtained was filtered, washed twice with MIK and finally with water, and dried under vacuum at about 70° C. The yield was 120 g equal to 65 wt. % of the theoretical. The measured HPLC purity was equal to 99.9%.

| $^1$H NMR | |
|---|---|
| Chemical Shift (ppm) | Multiplicity |
| 2.23 | Singlet |
| 3.31 | Doublet of doublets |
| 3.60 | Triplet |
| 4.00-4.15 | Multiplet |
| 4.81-4.92 | Multiplet |
| 6.56 | Singlet |
| 6.59 | Singlet |
| 7.53 | Singlet |

| $^{13}$C NMR |
|---|
| Chemical Shift (ppm) |
| 20.9 |
| 41.4 |
| 68.4 |
| 73.5 |
| 112.3 |
| 122.5 |
| 138.6 |
| 158.1 |
| 158.5 |

Example 2

Preparation of Metaxalone in Toluene and N-Methylpyrrolidone (NMP)

A 1-liter round-bottom flask was charged with about 180 ml of toluene, 100.3 g of m-xylenol, 20 ml of NMP, 1.0 g of triethylbenzylammonium chloride (TEBAC) and 0.40 g of NaOH. The reaction solution was heated to about 40° C. and kept at this temperature for about 30 minutes.

Then, 81.4 g of triglycidyl isocyanurate (TGIC) was added and the reaction solution was heated to 100° C. in about 3 hours, with a constant rate of temperature increase of about 0.33° C./min.

After that time, a further 0.8 g of NaOH were added to the reaction solution, it was heated to 118° C. at a constant rate of temperature increase of about 1.00° C./min and kept at this temperature for about 90 minutes.

Then the reaction solution was diluted with about 70 ml of toluene, and cooled to a temperature between 0° and 5° C. The metaxalone product was recovered by filtration, and purified by treatment with about 360 ml of toluene at 40° C.

The metaxalone thus obtained was filtered, washed twice with toluene and finally with water, and dried under vacuum at about 70° C. The yield was 115 g, equal to 63 wt. % of the theoretical. The measured HPLC purity was equal to 99.9%.

| $^1$H NMR | |
|---|---|
| Chemical Shift (ppm) | Multiplicity |
| 2.23 | Singlet |
| 3.31 | Doublet of doublets |
| 3.60 | Triplet |
| 4.00-4.15 | Multiplet |
| 4.81-4.92 | Multiplet |
| 6.56 | Singlet |
| 6.59 | Singlet |
| 7.53 | Singlet |

| $^{13}$C NMR |
|---|
| Chemical shift (ppm) |
| 20.9 |
| 41.4 |
| 68.4 |
| 73.5 |
| 112.3 |
| 122.5 |
| 138.6 |
| 158.1 |
| 158.5 |

Example 3

Preparation of Metaxalone in Xylene and Dimethylformamide (DMF)

A 1-liter round-bottom flask was charged with about 100 ml of xylene, 52.7 g of m-xylenol, 11 ml of DMF, 0.524 g of triethylbenzylammonium chloride (TEBAC) and 0.212 g of NaOH. The reaction solution was heated to about 40° C. and kept at this temperature for about 30 minutes.

Then, 42.7 g of triglycidyl isocyanurate (TGIC) was added and the reaction solution was heated to 100° C. in about 3 hours, with a constant rate of temperature increase of about 0.33° C./min.

After that time, a further 0.432 g of NaOH was added to the reaction solution, it was heated to 140° C. at a constant rate of temperature increase of about 1.00° C./min and kept at this temperature for about 90 minutes.

Then the reaction solution was diluted with about 40 ml of xylene, and cooled to a temperature of about 5° C. The metaxalone product was recovered by filtration, and purified by treatment with about 300 ml of xylene at 50° C.

The metaxalone thus obtained was filtered, washed twice with xylene and finally with water, and dried under vacuum at about 70° C. The yield was 57 g, equal to 60 wt. % of the theoretical. The measured HPLC purity was equal to 99.8%.

| $^1$H NMR | |
|---|---|
| Chemical Shift (ppm) | Multiplicity |
| 2.23 | Singlet |
| 3.31 | Doublet of doublets |
| 3.60 | Triplet |
| 4.00-4.15 | Multiplet |
| 4.81-4.92 | Multiplet |
| 6.56 | Singlet |
| 6.59 | Singlet |
| 7.53 | Singlet |

| $^{13}$C NMR |
|---|
| Chemical Shift (ppm) |
| 20.9 |
| 41.4 |
| 68.4 |
| 73.5 |
| 112.3 |
| 122.5 |
| 138.6 |
| 158.1 |
| 158.5 |

Example 4

Analysis of Impurities

Three samples of metaxalone obtained by the method described in examples 1, 2 and 3 respectively were analysed, for determination of genotoxic impurities containing epoxides represented by compounds of formula (VII) and (VIII) described above, using the method described hereunder.

1 mg of the sample of metaxalone was dissolved in 1 ml of a mixture of water:acetonitrile:formic acid in proportions by volume 50:50:2. The sample solution was stable at room temperature (25° C.) for at least 24 hours. The resultant solution was injected into an instrument for HPLC coupled to a tandem mass spectrometer. Chromatographic separation was obtained with a C18 reverse-phase analytical column. The eluate was analysed by mass spectrometry in so-called "positive ions" mode using the technique designated MRM (Multiple Reaction Monitoring).

The equipment used comprised a Perkin-Elmer series 200 micropump, a Perkin-Elmer series 200 automatic sampler, an Applied Biosystems API3000 LC/MS/MS mass spectrometer equipped with a TurbolonSpray® source, the whole controlled by the Applied Biosystems Analyst software management program.

The following Table 1 shows the operating conditions of the HPLC equipment.

TABLE 1

| | |
|---|---|
| Analytical column | Discovery HS C18, 3 μm 7.5 × 4.6 mm Batch number 94633-04 Cat number 569251-U, Supelco |

TABLE 1-continued

| | |
|---|---|
| Mobile phase | Solvent A, water with 0.1% formic acid |
| | Solvent B, acetonitrile with 0.1% formic acid |
| Flow | 1.5 ml/min |
| Elution | Gradient elution (*) |
| Volume injected | 100 μl |
| Analysis time | 14 minutes |
| Injector washing phase | Water: acetonitrile 900:10 (v/v) with 0.5% formic acid |
| Flow to MS | 400 μl/min |
| Retention times | |
| TGIC | 1.5 min |
| Metaxalone | 4.5 min |
| Compound VII | 6.5 min |
| Compound VIII | 8.8 min |
| Flow program | |
| Phase 0; 0-2 min | To the mass spectrometer |
| Phase 1; 2-5 min | Wasted |
| Phase 2; 5-14 min | To the mass spectrometer |

(*) The gradient elution program envisaged the following phases:

| | Solvent A (%) | Solvent B (%) |
|---|---|---|
| Phase 0; 0-2 min | 70 | 30 |
| Phase 1; 2-10 min | 70 | 30 |
| Phase 2; 10-10.1 min | 20 | 80 |
| Phase 3; 10.1-14 min | 70 | 30 |

The following Table 2 shows the operating conditions of the equipment for tandem mass spectrometry.

TABLE 2

| | |
|---|---|
| Ionization | ESI, positive ions mode |
| Turbo-gas temperature | 550° C. |
| Ionization voltage IS | 5500 V |
| Focusing potential FP | 200 V |
| Entry potential EP | 10 V |
| Gas nebulizer NEB | 10 |
| Curtain gas CUR | 15 |
| Collision gas CAD | 2 |
| Collision Cell Exit Potential CXP | 15 |
| Declustering potential | 30 V |
| Collision energy | 23 V |
| Acquisition mode | MRM(*) |

(*) The details of the MRM acquisition mode are given in the following table

| | Q1 MS (amu)* | Q3 MS (amu)* | Retention time (msec) |
|---|---|---|---|
| TGIC | 298.1 | 129.9 | 200 |
| Compound VII | 420.0 | 298.0 | 200 |
| Compound VIII | 542.0 | 420.0 | 200 |

*Atomic mass unit

The linearity of the method was verified from 0.05 to 2 ppm for all the analytes with a correlation coefficient, calculated by the method of least squares with linear regression, equal to 0.9998.

The accuracy of the method for compound VII was typically 90% at 0.05 ppm, 98% at 0.5 ppm and 97% at 2 ppm.

The accuracy of the method for compound VIII was typically 110% at 0.05 ppm, 98% at 0.5 ppm and 95% at 2 ppm.

The precision, measured as relative standard deviation (RSD), for compound VII was typically 6.1% at 0.05 ppm, 1% at 0.5 ppm and 1.7% at 2 ppm.

The precision, measured as relative standard deviation (RSD), for compound VIII was typically 10.1% at 0.05 ppm, 7.3% at 0.5 ppm and 3.7% at 2 ppm.

The limit of detection (LOD) was determined as 0.0013 ppm for TGIC, 0.01 ppm for compound (VII) and 0.02 ppm for compound (VIII) with respect to the signal/noise ratio (S/N) from the formula:

$$LOD = 3 \times S/N$$

The results are presented in the following Table 3.

TABLE 3

|  | TGIC | Compound VII | Compound VIII |
| --- | --- | --- | --- |
| Sample 1 | <0.0013 | <0.01 ppm | <0.1 ppm |
| Sample 2 | <0.0013 | <0.01 ppm | <0.1 ppm |
| Sample 3 | <0.0013 | <0.01 ppm | <0.1 ppm |

The invention claimed is:

1. A method of preparation of metaxalone having the following structural formula (I):

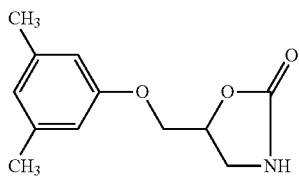

comprising reaction of triglycidyl isocyanurate (TGIC) of formula (III)

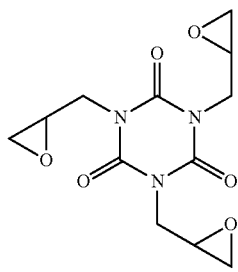

with m-xylenol of formula (V):

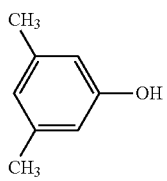

characterized in that said reaction is carried out in a solvent mixture comprising a first solvent selected from the group consisting of aprotic polar solvents with dielectric constant greater than or equal to 30 and a second solvent selected from the group consisting of apolar solvents and aprotic polar solvents with dielectric constant below 30, said solvent mixture comprising from 5 to 40 wt. % of said first solvent and from 95 to 60 wt. % of said second solvent, adding the TGIC at a temperature between 30° C. and 50° C. and after adding the TGIC raising the temperature of the reaction solution to a value between 80° C. and 180° C. in a time between 120 and 180 minutes at a rate of increase not greater than 1.25° C. per minute.

2. The method of preparation of metaxalone according to claim 1, characterized in that said aprotic polar solvent is selected from the group consisting of N-methylpyrrolidone, dimethylformamide, dimethylsulphoxide, hexamethylphosphoramide, dimethylacetamide and acetonitrile.

3. The method of preparation of metaxalone according to claim 1, characterized in that said apolar solvent is selected from the group consisting of cyclohexane, heptane, benzene, toluene, xylene, mesitylene, naphthalene, chlorobenzene, chloroxylene, chloroform, propyl ether, isopropyl ether, butyl ether, pentyl ether, benzylethyl ether, tetrahydrofuran (THF) and 2-methyl tetrahydrofuran.

4. The method of preparation of metaxalone according to claim 1, characterized in that said aprotic polar solvent with dielectric constant below 30 is selected from the group consisting of acetone, methyl ethyl ketone, methyl butyl ketone, methyl isobutyl ketone, 2-pentanone, cyclopentanone and 2-heptanone.

5. The method of preparation of metaxalone according to claim 1, characterized in that said solvent mixture comprises from 10 to 30 wt. %, of said first solvent and from 90 to 70 wt. %, of said second solvent.

6. The method of preparation of metaxalone according to claim 1, characterized in that the reaction solution further comprises an organic or inorganic base and a phase transfer catalyst.

7. The method of preparation of metaxalone according to claim 6, characterized in that the reaction solution comprises an amount of said organic or inorganic base between 3 and 10 mol. % relative to the molar amount of TGIC present in said reaction solution.

8. The method of preparation of metaxalone according to claim 6, characterized in that the reaction solution comprises an amount of said phase transfer catalyst between 0.5 and 5 mol. % relative to the amount of TGIC present in said reaction solution.

9. The method of preparation of metaxalone according to claim 6, characterized in that the solution comprising m-xylenol, the base and the phase transfer catalyst dissolved in the solvent mixture is heated to a temperature between 35° C. and 45° C., before adding the TGIC.

10. The method of preparation of metaxalone according to claim 6, characterized in that the reaction solution comprises an inorganic base selected from the group consisting of oxides of alkali metals, hydroxides of alkali metals, carbonates of alkali metals, and carbonates of alkaline earth metals.

11. The method of preparation of metaxalone according to claim 6, characterized in that the phase transfer catalyst is a halide of quaternary ammonium or phosphonium.

12. The method of preparation of metaxalone according to claim 6, characterized in that the reaction solution comprises an amount of said organic or inorganic base between 3 and 6 mol. % relative to the molar amount of TGIC present in said reaction solution.

13. The method of preparation of metaxalone according to claim 6, characterized in that the reaction solution comprises an amount of said phase transfer catalyst between 1 and 3 mol. % relative to the amount of TGIC present in said reaction solution.

14. The method of preparation of metaxalone according to claim 1, characterized in that, after adding TGIC, the reaction solution is gradually heated at a rate of increase not greater than 1.00° C. per minute.

15. The method of preparation of metaxalone according to claim 14, where at the end of the phase of gradual temperature rise, an amount of base between 3 and 10 mol. % relative to the molar amount of TGIC present in the starting reaction solution, is added to the starting reaction solution.

16. The method of preparation of metaxalone according to claim 14, where at the end of the phase of gradual temperature rise, an amount of base between 5 and 8 mol. % relative to the molar amount of TGIC present in the starting reaction solution, is added to the starting reaction solution.

17. The method of preparation of metaxalone according to claim 1, characterized in that said aprotic polar solvent is selected from the group consisting of N-methylpyrrolidone and dimethylformamide.

18. The method of preparation of metaxalone according to claim 1, characterized in that said apolar solvent is selected from the group consisting of toluene and xylene.

19. The method of preparation of metaxalone according to claim 1, characterized in that said aprotic polar solvent with dielectric constant below 30 is methyl isobutyl ketone.

20. The method of preparation of metaxalone according to claim 1, characterized in that, after adding TGIC, the reaction solution is gradually heated at a rate of increase not greater than 0.75° C. per minute.

* * * * *